United States Patent
Chang

(10) Patent No.: US 9,877,671 B2
(45) Date of Patent: Jan. 30, 2018

(54) APPARATUS, SYSTEMS, AND METHODS FOR DETECTING CONGENITAL HEART DISEASE IN NEWBORNS

(71) Applicant: LOS ANGELES BIOMEDICAL RESEARCH INSTITUTE AT HARBOR-UCLA MEDICAL CENTER, Torrance, CA (US)

(72) Inventor: Ruey-Kang Chang, Diamond Bar, CA (US)

(73) Assignee: LOS ANGELES BIOMEDICAL RESEARCH INSTITUTE AT HARBOR—UCLA MEDICAL CENTER, Torrance, CA (US)

( * ) Notice: Subject to any disclaimer, the term of this patent is extended or adjusted under 35 U.S.C. 154(b) by 53 days.

(21) Appl. No.: 14/515,820

(22) Filed: Oct. 16, 2014

(65) Prior Publication Data
US 2015/0112171 A1    Apr. 23, 2015

Related U.S. Application Data

(60) Provisional application No. 61/893,804, filed on Oct. 21, 2013.

(51) Int. Cl.
*A61B 5/1455* (2006.01)
*A61B 5/00* (2006.01)

(52) U.S. Cl.
CPC ........ *A61B 5/14552* (2013.01); *A61B 5/6825* (2013.01); *A61B 5/6829* (2013.01);
(Continued)

(58) Field of Classification Search
CPC ............ A61B 5/14551; A61B 5/14552; A61B 5/6826; A61B 5/6838; A61B 5/1495
See application file for complete search history.

(56) References Cited

U.S. PATENT DOCUMENTS

| 5,125,403 A | 6/1992 | Culp |
| 5,842,982 A | 12/1998 | Mannheimer |

(Continued)

FOREIGN PATENT DOCUMENTS

| CN | 1657007 | 8/2005 |
| WO | WO2005065540 | 7/2005 |

OTHER PUBLICATIONS

Chang, R.K., et al., "Missed Diagnosis of Critical Congenital Heart Disease", Arch. Pediatr. Adolesc. Med., 2008, 162(10):969-974.

(Continued)

*Primary Examiner* — Eric Winakur
*Assistant Examiner* — Marjan Fardanesh
(74) *Attorney, Agent, or Firm* — Pillsbury Winthrop Shaw Pittman, LLP

(57) ABSTRACT

Apparatus configured to detect congenital heart disease (CHD) in newborns may comprise a body with a cavity configured to receive a hand or foot of a newborn. Sensor pairs of the apparatus may be configured scan such that the best signals can be selected, which can accommodate for movements of the newborn and/or facilitate impartialness as to which body part is inserted in the apparatus. Positions of the sensor pairs may be adjusted to ensure contact with the newborn's skin. A disposable cover may protect the newborn's skin from contacting the apparatus. The apparatus may include a pressure device so that CHD threshold values can be adjusted for different altitudes. The apparatus may integrate with electronic medical record (EMR) systems.

7 Claims, 8 Drawing Sheets

(52) U.S. Cl.
CPC .......... *A61B 5/6843* (2013.01); *A61B 5/0015* (2013.01); *A61B 5/4538* (2013.01); *A61B 2503/045* (2013.01)

(56) References Cited

U.S. PATENT DOCUMENTS

| | | | |
|---|---|---|---|
| 5,978,691 A | 11/1999 | Mills | |
| 6,047,201 A | 4/2000 | Jackson | |
| 6,334,065 B1 | 12/2001 | Al-Ali et al. | |
| 6,470,199 B1 | 10/2002 | Kopotic et al. | |
| 6,510,331 B1* | 1/2003 | Williams | A61B 5/14542 600/323 |
| 6,615,065 B1* | 9/2003 | Barrett | A61B 5/6814 600/323 |
| 7,171,251 B2 | 1/2007 | Sarussi et al. | |
| 7,190,987 B2 | 3/2007 | Lindekugel et al. | |
| 8,740,792 B1* | 6/2014 | Kiani | A61B 5/7296 600/301 |
| 2002/0028990 A1 | 3/2002 | Shepherd et al. | |
| 2002/0035317 A1* | 3/2002 | Cheng | A61B 5/14546 600/322 |
| 2002/0035927 A1* | 3/2002 | Kutt | A61G 10/02 96/111 |
| 2002/0133067 A1 | 9/2002 | Jackson | |
| 2004/0039272 A1* | 2/2004 | Abdul-Hafiz | A61B 5/14552 600/322 |
| 2004/0116787 A1 | 6/2004 | Schnall | |
| 2004/0260161 A1 | 12/2004 | Melker et al. | |
| 2005/0197551 A1 | 9/2005 | Ali-Ali et al. | |
| 2006/0069319 A1 | 3/2006 | Elhag et al. | |
| 2006/0189871 A1 | 8/2006 | Al-Ali et al. | 600/476 |
| 2007/0088341 A1 | 4/2007 | Skiba et al. | |
| 2008/0009754 A1 | 1/2008 | Chang | |
| 2008/0071155 A1 | 3/2008 | Kiani | |
| 2011/0015498 A1 | 1/2011 | Mestrovic et al. | |
| 2012/0016219 A1* | 1/2012 | Fujii | A61B 5/14552 600/324 |
| 2012/0046532 A1* | 2/2012 | Chang | A61B 5/02438 600/324 |
| 2012/0253153 A1* | 10/2012 | Trumble | A61B 5/14551 600/324 |
| 2013/0125891 A1* | 5/2013 | Eddy | A61M 16/204 128/204.23 |

OTHER PUBLICATIONS

Chang, R.K., et al., "Screening Newborns for Congenital Heart Disease with Pulse Oximetry; Survey of Pediatric Cardiologists", Pediatr.Cardiol, 2009, 30(1):20-25.

Hoffman, J.I., "It is Time for Routine Neonatal Screening by Pulse Oximetry", Neonatology, 2011, 99(1):1-9.

Mahle, W.T., et al., "Role of Pulse Oximetry in Examining Newborns for Congenital Heart Disease: A Scienctific Statement from the American Heart Association and American Academy of Pediatrics", Circulation, 2009, 120(5):447-458.

Roan, S., "Congenital Heart Disease Screening Recommended for Newborns", Los Angeles Times, Health Section, Aug. 21, 2011, 4 pages.

* cited by examiner

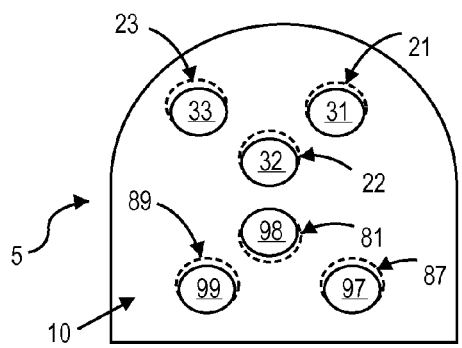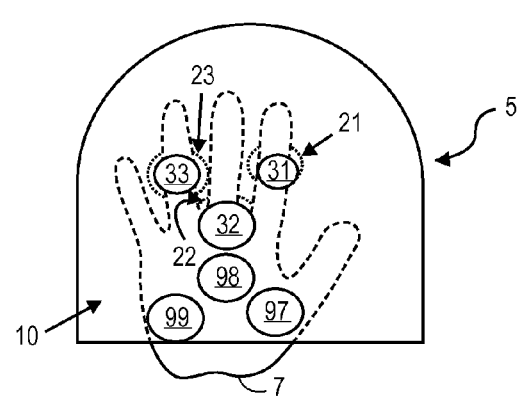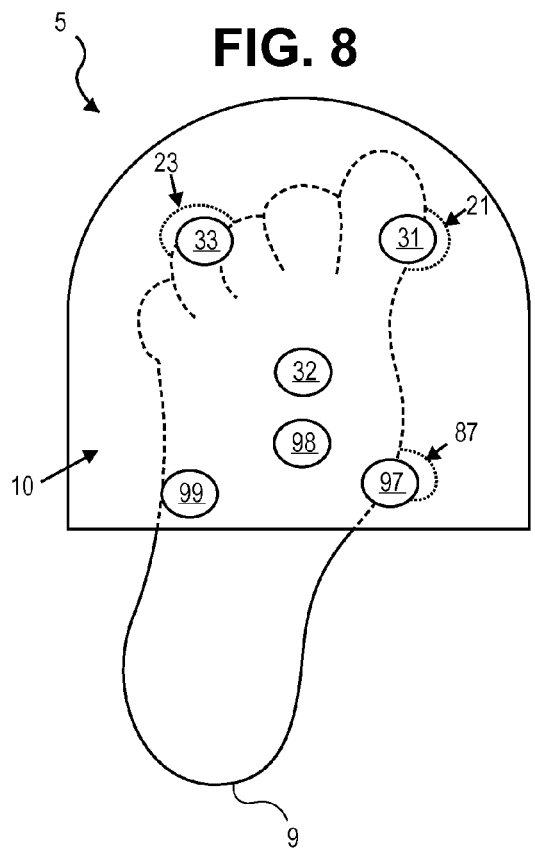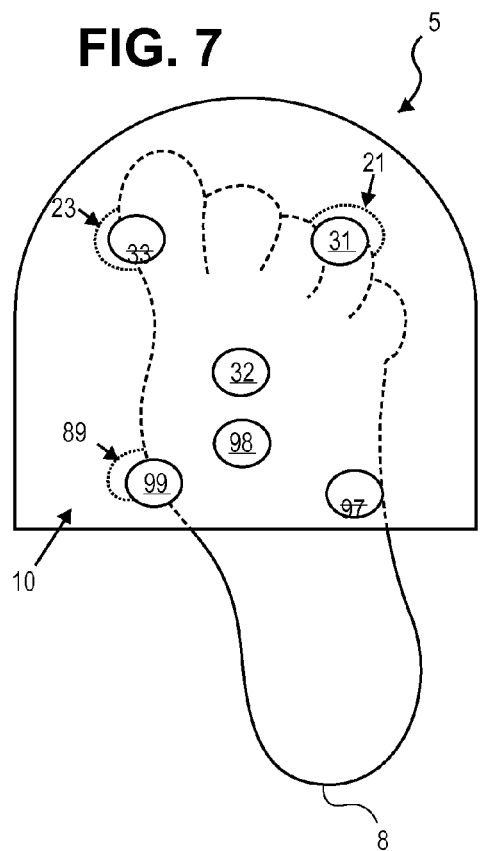

ND METHODS
APPARATUS, SYSTEMS, AND METHODS FOR DETECTING CONGENITAL HEART DISEASE IN NEWBORNS

RELATED APPLICATIONS

This application claims the benefit of priority of Application Ser. No. 61/893,804, filed Oct. 21, 2013, which is expressly incorporated herein by reference in its entirety.

FIELD OF THE DISCLOSURE

This disclosure relates to apparatus, systems, and methods for detecting congenital heart disease (CHD) in newborns using pulse oximetry.

BACKGROUND

Pulse oximetry can be used to measure the arterial oxygen saturation of hemoglobin (SpO2) and pulse rate of a patient. Measurement of these characteristics is generally accomplished by use of a non-invasive electro-optical sensor which scatters red and infrared lights through an arterially perfused portion of the patient's tissue. The sensor then detects the differential amounts of red and infrared light that are photoelectrically absorbed by the tissue. Stated otherwise, the sensor detects the amount of red and infrared light that passes through the patient's tissue. The differential amounts absorbed are then used to calculate SpO2.

Pulse oximetry is commonly used as a monitoring device in emergency departments, intensive care units, observational units, and operating rooms. Most pulse oximeter probes are designed for prolonged and continuous monitoring of a patient's SpO2 and pulse rate. These probes are generally shaped as a clip for a finger or toe.

Congenital heart disease (CHD) affects 8 per 1,000 newborns and is one of the most common and serious types of birth defects. If diagnosed early, CHD can be managed with palliation or successful surgical repair for the majority of CHD-affected newborns. However, a missed or delayed diagnosis can be life threatening or result in long-term morbidities for CHD-affected newborns. Current clinical practice for detecting CHD in newborns relies on a clinician performing a physical examination before the child's discharge from the nursery. However, a significant number of newborns with CHD are missed by physical examination.

In recent years, health care professionals have found pulse oximetry an important screening tool to aid clinical examination for detecting some severe forms of CHD. In a 2007 survey of 1,086 pediatric cardiologists, the majority of respondents supported a mandate for universal screening by pulse oximetry before newborn discharge. In 2009, the American Heart Association and American Academy of Pediatrics jointly issued a scientific statement recommending routine pulse oximetry screening on the foot of asymptomatic newborns after 24 hours of life, but before hospital discharge. In 2011, the Secretary of Health and Human Services approved the addition of screening newborns for critical CHD by pulse oximetry to the Recommended Uniform Screening Panel.

The most commonly used pulse oximetry sensors require attachment to the fingers or toes of a patient by some sort of clip. For adults and older children, clip-type pulse oximetry sensors are typically not a problem. The fingers and toes of a newborn, however, are much too small for the clip-type pulse oximetry sensors that are commonly used on older children and adults to fit properly. Conventional approaches to fitting a clip-type pulse oximetry sensor on a newborn's finger/toe or hand/foot includes securing the sensor in place with adhesives or Velcro. Sensors secured with adhesives or Velcro, however, are generally single-use and therefore add substantial expenses to the universal screening of all newborns at hospital discharge. Moreover, securing pulse oximetry sensors on newborns in such a manner takes a considerable amount of time, which adds difficulty to the bigger picture of screening a large number of newborns. Furthermore, sensors that are secured to newborns with adhesives or Velcro are prone to motion artifacts and signal interferences from ambient light, both of which are unwanted in newborn screenings given that accurate and reliable results are needed to diagnose CHD-affected newborns.

SUMMARY

One aspect of the disclosure relates to apparatus configured to detect congenital heart disease (CHD) in newborns. The apparatus may comprise a body, sensor pairs, and a pressure device. The body may comprise a cavity configured to receive a portion of a hand or a foot of a newborn. The cavity may substantially encompass the portion of the newborn's hand or foot when the portion the newborn's hand or foot is received by the cavity. The sensor pairs may include a first sensor pair. Individual ones of the sensor pairs may be configured to provide detection signals conveying information associated with oxygen saturation. The first sensor pair may include a first light emitter and a corresponding first light detector disposed at opposing locations in the cavity of the body such that, when the portion of the newborn's hand or foot is inside the cavity, light from the first light emitter that passes through the newborn's hand or foot is detected by the first light detector. The pressure device may be configured to provide a pressure signal conveying information associated with an ambient air pressure in an environment surrounding the apparatus.

Another aspect of the disclosure relates to apparatus configured to detect CHD in newborns. The apparatus may comprise a body, sensor pairs, and one or more processors configured to execute computer program modules. The body may comprise a cavity configured to receive a portion of a hand or a foot of a newborn. The cavity may substantially encompass the portion of the newborn's hand or foot when the portion the newborn's hand or foot is received by the cavity. The sensor pairs may include a first sensor pair. Individual ones of the sensor pairs may be configured to provide detection signals conveying information associated with oxygen saturation. The first sensor pair may include a first light emitter and a corresponding first light detector disposed at opposing locations in the cavity of the body such that, when the portion of the newborn's hand or foot is inside the cavity, light from the first light emitter that passes through the newborn's hand or foot is detected by the first light detector. The computer program modules may comprise an oxygen saturation determination module, a CHD determination module, and an electronic medical record (EMR) interface module. The oxygen saturation determination module may be configured to determine a saturation value indicative of oxygen saturation of the newborn based on one or more detection signals provided by the sensor pairs. The CHD determination module may be configured to determine a presence of CHD in the newborn responsive to the saturation value breaching a threshold saturation value. The EMR interface module may be configured to access an EMR associated with the newborn.

Yet another aspect of the disclosure relates to apparatus configured to detect CHD in newborns. The apparatus may comprise a body, sensor pairs, and one or more processors configured to execute computer program modules. The body may comprise a cavity configured to receive a portion of a hand or a foot of a newborn. The cavity may substantially encompass the portion of the newborn's hand or foot when the portion the newborn's hand or foot is received by the cavity. The sensor pairs may include a first sensor pair. Individual ones of the sensor pairs may be configured to provide detection signals conveying information associated with oxygen saturation. The first sensor pair may include a first light emitter and a corresponding first light detector disposed at opposing locations in the cavity of the body such that, when the portion of the newborn's hand or foot is inside the cavity, light from the first light emitter that passes through the newborn's hand or foot is detected by the first light detector. The computer program modules may comprise a sensor selection module, an oxygen saturation determination module, and a CHD determination module. The sensor selection module may be configured to select a subset of the detection signals provided by the sensor pairs based on a determination of which body part of the newborn is received by the cavity. The body part may be a portion of one of a left foot, a right foot, a left hand, or a right hand. The oxygen saturation determination module may be configured to determine a saturation value indicative of oxygen saturation of the newborn based on the selected subset of the detection signals. The CHD determination module may be configured to determine a presence of CHD in the newborn responsive to the saturation value breaching a threshold saturation value.

Still another aspect of the disclosure relates to apparatus configured to detect CHD in newborns. The apparatus may comprise a body, sensor pairs, and a sensor positioning device. The body may comprise a cavity configured to receive a portion of a hand or a foot of a newborn. The cavity may substantially encompass the portion of the newborn's hand or foot when the portion the newborn's hand or foot is received by the cavity. The sensor pairs may include a first sensor pair. Individual ones of the sensor pairs may be configured to provide detection signals conveying information associated with oxygen saturation. The first sensor pair may include a first light emitter and a corresponding first light detector disposed at opposing locations in the cavity of the body such that, when the portion of the newborn's hand or foot is inside the cavity, light from the first light emitter that passes through the newborn's hand or foot is detected by the first light detector. The sensor positioning device may be configured to reposition individual ones of the two or more sensor pairs responsive to the portion of the newborn's hand or foot being received by the cavity. Repositioning the first sensor pair may include moving one or both of the first light emitter or the first light detector such that one or both of the first light emitter or the first light detector contact skin of the portion of the newborn's hand or foot.

Even another aspect of the disclosure relates to apparatus configured to detect CHD in newborns. The apparatus may comprise a body, sensor pairs, and a disposable cover. The body may comprise a cavity configured to receive a portion of a hand or a foot of a newborn. The cavity may substantially encompass the portion of the newborn's hand or foot when the portion the newborn's hand or foot is received by the cavity. The sensor pairs may include a first sensor pair. Individual ones of the sensor pairs may be configured to provide detection signals conveying information associated with oxygen saturation. The first sensor pair may include a first light emitter and a corresponding first light detector disposed at opposing locations in the cavity of the body such that, when the portion of the newborn's hand or foot is inside the cavity, light from the first light emitter that passes through the newborn's hand or foot is detected by the first light detector. The disposable cover may be configured to line the cavity to protect skin on the portion of the newborn's hand or foot that is received by the cavity. The disposable cover may include transparent portions and opaque portions. The transparent portions may be configured to allow light to pass between individual sensor pairs. The opaque portions may be configured to block light from passing between adjacent sensor pairs.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 5 illustrates the positions of emitters and detectors inside the apparatus illustrated in FIG. 2, in accordance with one or more implementations.

FIG. 6 illustrates the under surface of the apparatus of FIG. 2 with a portion of a newborn's right hand inserted into the apparatus, in accordance with one or more implementations.

FIG. 7 illustrates the under surface of the apparatus of FIG. 2 with a portion of a newborn's left foot inserted into the apparatus, in accordance with one or more implementations.

FIG. 8 illustrates the under surface of the apparatus of FIG. 2 with a portion of a newborn's right foot inserted into the apparatus, in accordance with one or more implementations.

DETAILED DESCRIPTION

Figure 1:
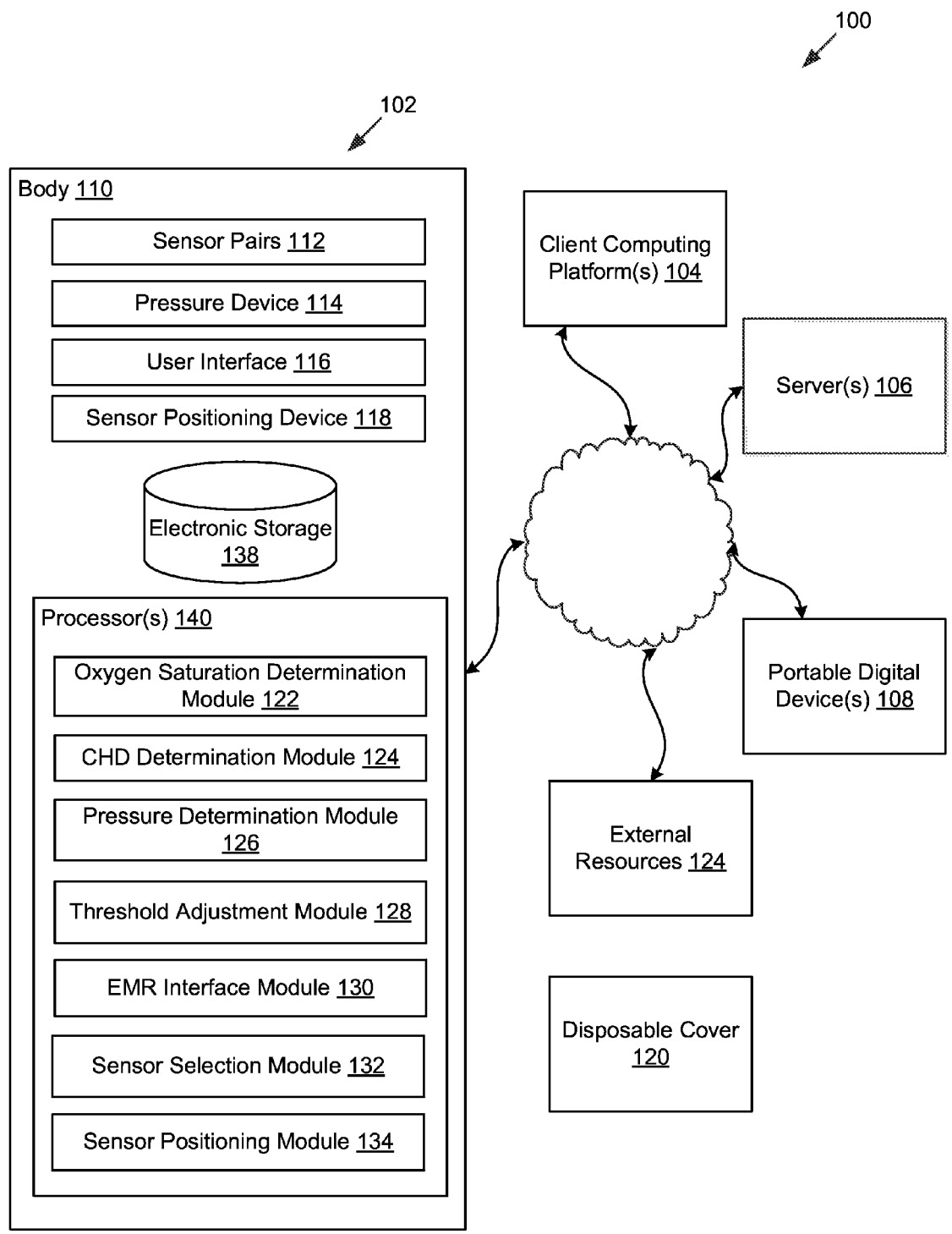
FIG. 1 illustrates a system configured for detecting CHD in newborns, in accordance with one or more implementations.

FIG. 1 illustrates a system 100 configured for detecting CHD in newborns, in accordance with one or more implementations. A newborn as used herein is only minutes, hours, days, or up to one month old. In some implementations, system 100 may include apparatus 102. The apparatus 102 may be configured to communicate with one or more client computing platforms 104, one or more servers 106, one or more portable digital devices 108, and/or other components of system 100 according to a peer-to-peer architecture, a client/server architecture, and/or other architectures. According to some implementations, users may access system 100 via client computing platform(s) 104, server(s) 106, and/or portable digital device(s) 108.

The apparatus 102 may be configured to detect or facilitate detection of CHD in newborns. The apparatus 102 may comprise a body comprising a cavity configured to receive a portion of a hand or a foot of a newborn. The cavity may substantially encompass the portion of the newborn's hand or foot when the portion the newborn's hand or foot is received by the cavity. The cavity may have a fixed size and/or a fixed shape. The cavity may be formed of a rigid material or a semi-rigid material.

Figure 2:
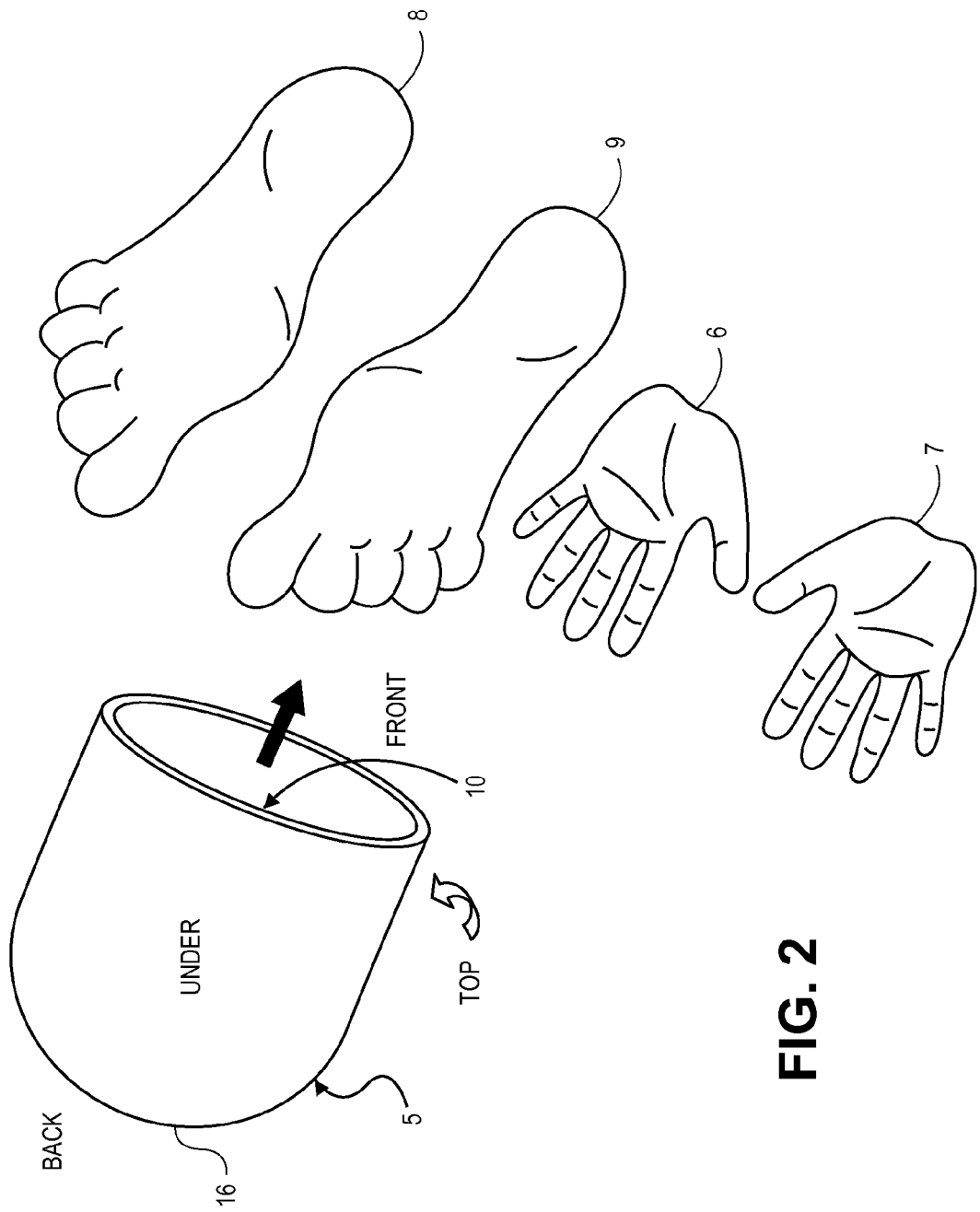
FIG. 2 illustrates an exemplary implementation of apparatus configured to detect or facilitate detection of CHD in newborns.

FIG. 2 illustrates an exemplary implementation of an apparatus 5, which may be the same as or similar to apparatus 102. In this implementation, apparatus 5 includes a tubular body defined by body 16, which may be the same as or similar to body 110. Body 16, as shown, has an open front end. The tubular body defines hollow space, volume, or chamber 10 sized to accommodate at least a portion of a newborn's left hand 6 (fingers first), right hand 7 (fingers first), left foot 8 (toes first), or right foot 9 (toes first) for signal acquisition.

In the implementation shown in FIG. 2, case 16 of apparatus 5 has a closed back end opposite the open front end of case 16. As illustrated, in one implementation, the closed back end has a dome shape. It is appreciated that other shapes are possible (e.g., flat, pyramidal, etc.). In some implementations, the back end may be open or partially open. It is further appreciated that, although case 16 of apparatus 5 is shown having a tubular shape, other shapes are possible (e.g., rectangular, etc.), so long as a portion of a newborn's hand or foot can fit inside.

Turning back to FIG. 1, apparatus 102 may comprise two or more sensor pairs 112, a pressure device 114, a user interface 116, a sensor positioning device 118, and/or other components. Individual ones of the sensor pairs 112 may be configured to provide detection signals conveying information associated with oxygen saturation. A given sensor pair may include a light emitter and a corresponding light detector. The light emitter and the light detector of a given sensor pair may be disposed at opposing locations in the cavity of body 100 such that, when the portion of the newborn's hand or foot is inside the cavity, light from the light emitter that passes through the newborn's hand or foot is detected by the light detector. According to various implementations, a given light emitter may be configured to provide light at a single wavelength, two or more discrete wavelengths (e.g., red light such as 660 nanometers (nm) and a light with infrared wavelength such as 940 nm), a range of wavelengths, and/or other wavelengths. In some implementations, light provided by a given light emitter may be modulated or continuous.

Figure 3:
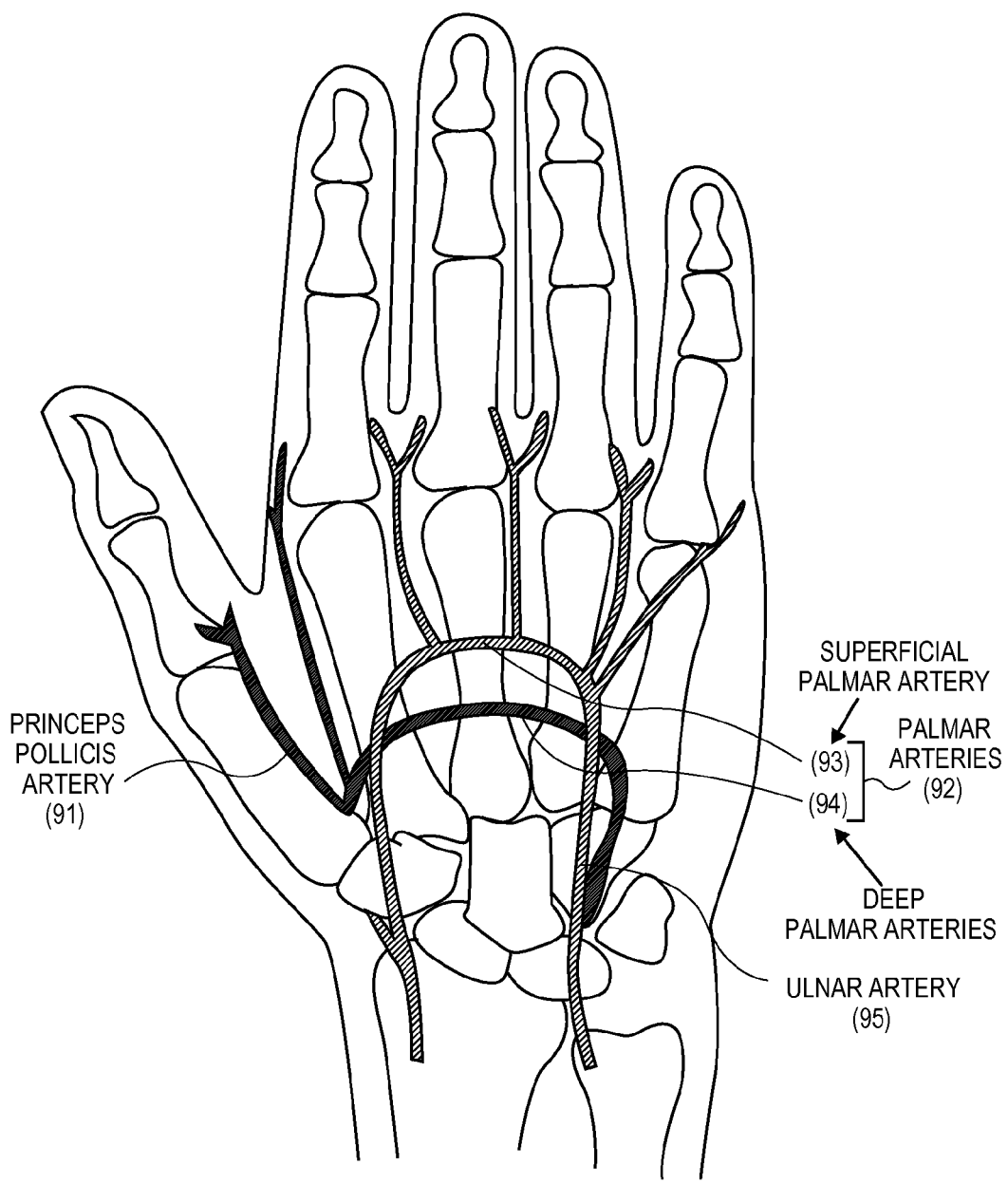
FIG. 3 illustrates the arterial blood supply of the right hand.

FIG. 3 is an anatomical illustration of the arterial blood supply of the right hand. The three major arteries in the hand are princeps pollicis artery 91 in the thumb, palmar arteries 92 in the center of the palm, and ulnar artery 95 in the medial aspect of the palm. Palmar arteries 92 include the superficial 93 and deep 94 palmar arteries that traverse the center of the palm. Those of skill in the art will understand that the anatomical illustration of the arterial blood supply of the left hand is a mirror image of FIG. 3.

Figure 4:
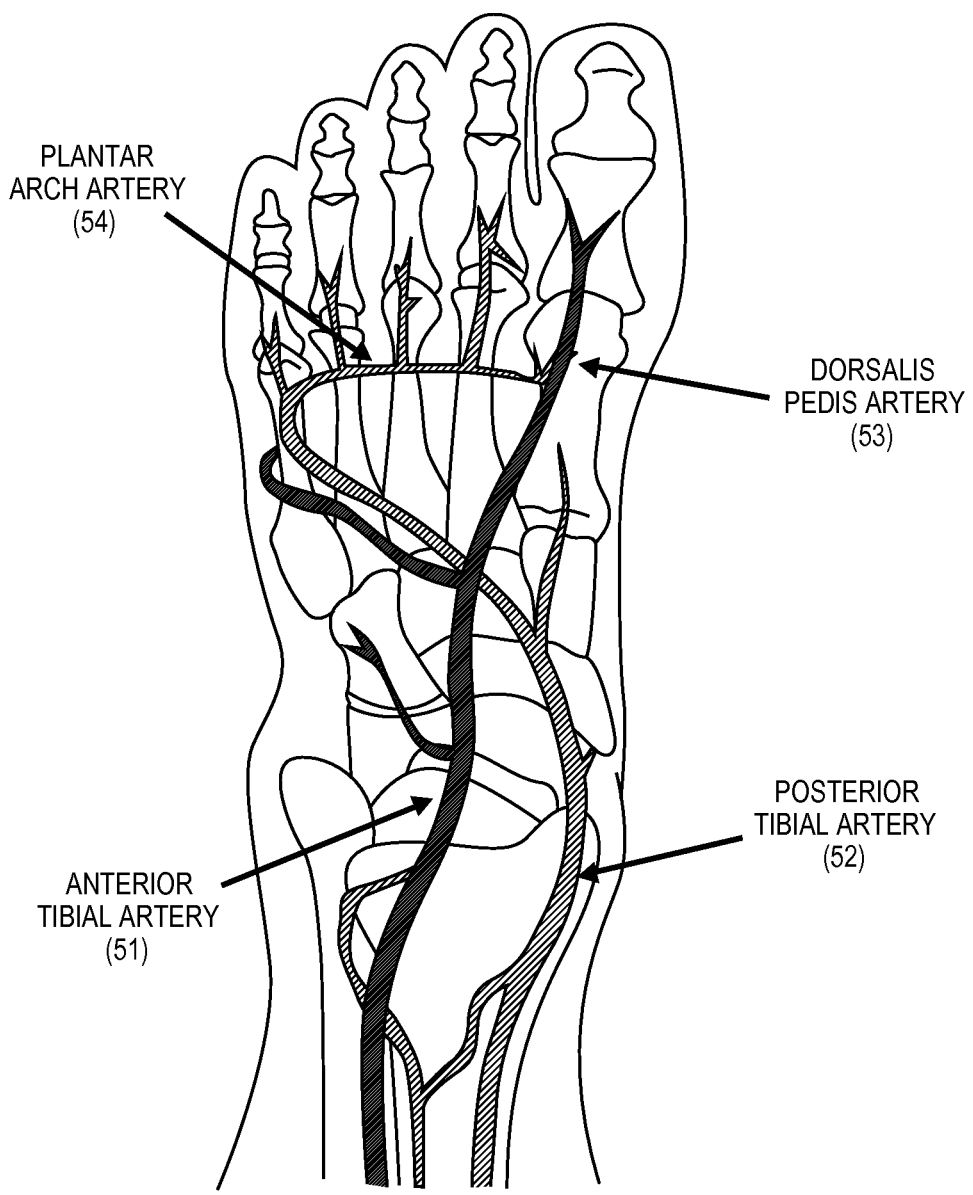
FIG. 4 illustrates the arterial blood supply of the left foot.

FIG. 4 is an anatomical illustration of the arterial blood supply of the left foot. The two major arteries to the foot are anterior tibial artery 51 and posterior tibial artery 52. Anterior tibial artery 51 branches to dorsalis pedis artery 53 which courses through the dorsal side of the foot to the first toe. Posterior tibial artery 52 courses through the ventral side of the foot and becomes plantar arch artery 54. Those of skill in the art will understand that the anatomical illustration of the arterial blood supply of the right foot is a mirror image of FIG. 4.

FIG. 5 is an illustration of sensor positions of apparatus 5, in accordance with one or more implementations. Each sensor has two positions, one for the emitter and one for the detector. That is, as a pair, a light emitter and corresponding light detector, in combination, comprise a single sensor pair. In one implementation, individual emitter/detector pairs are disposed on opposite sides of chamber 10 such that for a given emitter/detector pair the emitter is disposed to chamber 10 across from and opposite to where the corresponding detector is coupled to chamber 10. FIG. 5 is a view from an underside surface of apparatus 5 and illustrates an implementation in which light detectors and light emitters are connected to the bottom and top of chamber 10, respectively. In an underside view of this implementation, the emitters are normally blocked from view by the detectors because the emitters are directly above the detectors. However, to aid in illustrating the implementation, each light emitter is offset from its corresponding light detector and represented by a circle with dashed lines. The detectors are represented by circles with solid lines. In one implementation, as illustrated in FIG. 5, apparatus 5 includes six sensors, or six emitter/detector pairs, namely 87/97, 88/98, 89/99, 21/31, 22/32, and 23/33. Each light emitter and corresponding light detector can be connected to a chamber 10 wall of apparatus 5 such that light can be emitted and detected in chamber 10. In one implementation, three emitter/detector pairs are for a hand, namely 87/97, 88/98, and 89/99, and three emitter/detector pairs are for a foot, namely 21/31, 22/32, and 23/33. Those of skill in the art will appreciate that there can be more or less than six pairs of light emitters and detectors. For example, in one implementation, the three pairs of emitters/detectors for the foot can be omitted. In another implementation, the three pairs of emitters/detectors for the hand can be omitted. It is appreciated that more combinations are possible, depending on the application. In one implementation, the light detectors are connected to the bottom of chamber 10 and the light emitters are connected to the top of chamber 10. For example, in one implementation, a detector of a first sensor is positioned in chamber 10 to detect or receive light passed through a portion of a hand or a foot and detector of a second sensor is positioned in chamber 10 to detect or receive light passed through a portion of the other of the hand or the foot such that the first sensor and the second sensor are together positioned to separately pass light through and to detect or receive the light that passed through each of a hand and a foot from a corresponding respective sensor emitter. In other words, in such a two sensor implementation, apparatus 5 can separately perform measurements on a hand and a foot.

FIG. 6 is a view from the underside surface of apparatus 5 with a portion of right hand 7 inserted into chamber 10. In this implementation, detectors 97, 98 and 99 are shown to contact the palmar surface of right hand 7 in anatomical locations where there are arterial pulses. Emitters 87, 88 and 89 are not visible from this perspective. FIG. 7 is a view from the underside surface of apparatus 5 with a portion of left foot 8 inserted into chamber 10. In this implementation, detectors 32 and 33 are shown to contact the ventral surface of left foot 8 in anatomical locations where there are arterial pulses. Detector 31 does not detect an arterial pulse when a newborn's left foot is inserted. Emitters 21, 22 and 23 are not visible from this perspective. FIG. 8 is a view from the underside surface of apparatus 5 with a portion of right foot 9 inserted into chamber 10. In this implementation, detectors 31 and 32 are shown to contact the ventral surface of right foot 9 in anatomical locations where there are arterial pulses. Detector 33 does not detect an arterial pulse when a newborn's right foot is inserted. Emitters 21, 22 and 23 are not visible from this perspective. It is appreciated that apparatus 5 can also accommodate a newborn's left hand.

In one implementation, referring to FIGS. 6-8, emitter/detector pair 21/31 are separately connected to case 16 and positioned inside chamber 10 to detect pulse signals from dorsalis pedis artery 53 of the first toe when a newborn's right foot is placed inside chamber 10 of apparatus 5 (FIG. 8). Emitter/detector pair 23/33 are separately connected to case 16 and positioned inside chamber 10 to detect pulse signals from dorsalis pedis artery 53 of the first toe when a newborn's left foot is placed inside chamber 10 of apparatus 5 (FIG. 7). Emitter/detector pair 22/32 are separately connected to case 16 and positioned inside chamber 10 to detect pulse signals from plantar arch artery 54 of the foot when either a newborn's right or left foot is placed inside chamber 10 (FIGS. 7-8). Emitter/detector pair 87/97 are separately connected to case 16 and positioned inside chamber 10 to detect pulse signals from princeps pollicis artery 91 of the thumb when a newborn's right hand is placed inside chamber 10 of apparatus 5 (FIG. 7). Emitter/detector pair 88/98 are separately connected to case 16 and positioned inside chamber 10 to detect pulse signals from palmar arteries 92 of the hand when a newborn's right hand is placed inside chamber 10 of apparatus 5 (FIG. 6). Emitter/detector pair 89/99 are separately connected to case 16 and positioned inside chamber 10 to detect pulse signals from ulnar artery 95 of the hand when a newborn's right hand is placed inside chamber 10 of apparatus 5 (FIG. 6). It is appreciated that apparatus 5 can also accommodate a newborn's left hand.

Figure 9:
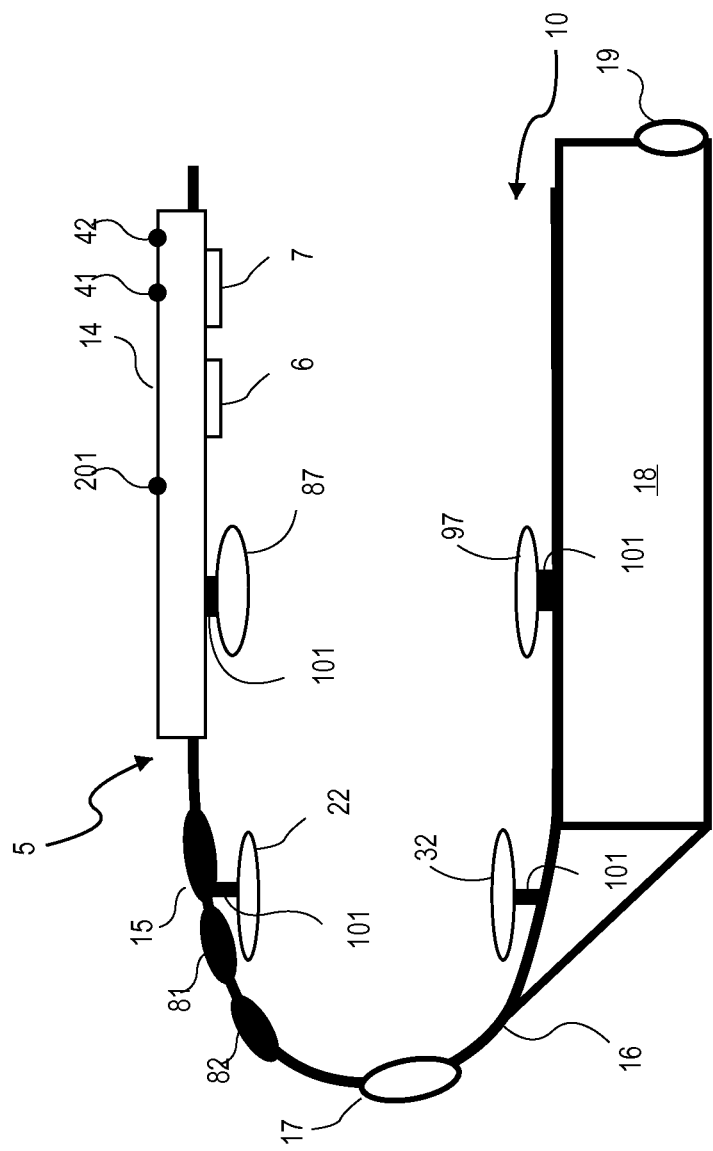
FIG. 9 illustrates a longitudinal sectional view of the apparatus of FIG. 2, in accordance with one or more implementations.
Figure 10:
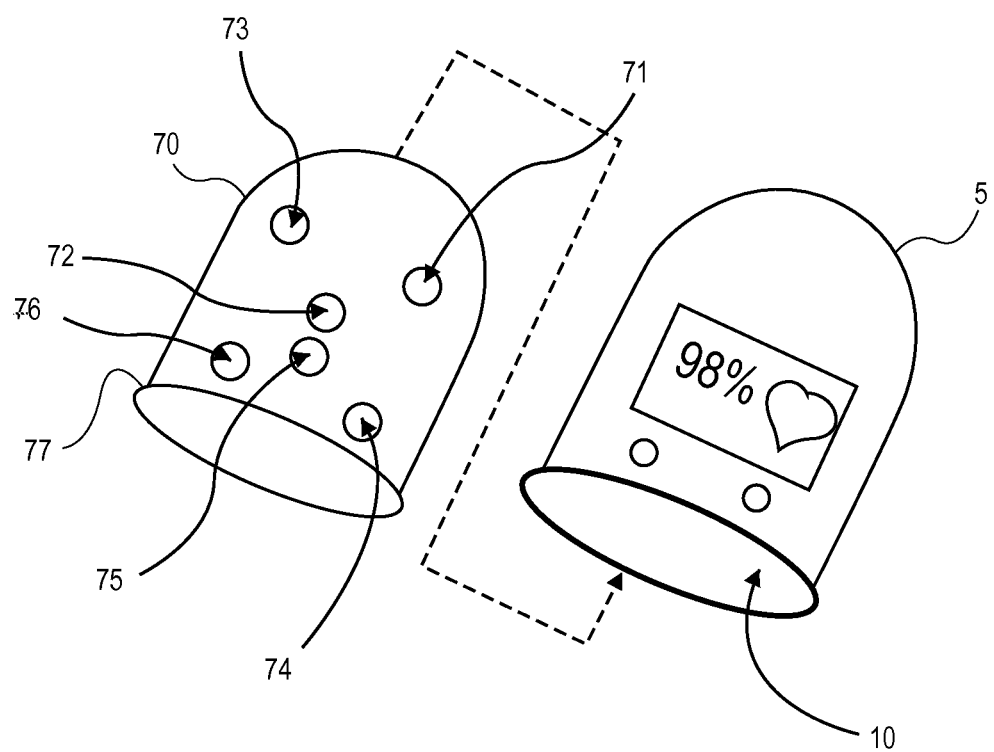
FIG. 10 illustrates a top side view illustration of a cover that can be positioned within the apparatus of FIG. 1, in accordance with one or more implementations.

FIG. 9 illustrates of a longitudinal sectional view of apparatus 5, in accordance with one or more implementations. In one implementation, light emitters are located on the top side of chamber 10 (as viewed), and the paired receivers are located on the bottom side directly opposite the paired emitters. For simplicity, FIG. 10 illustrates one emitter/detector pair 22/32 for a foot and one emitter/detector pair 87/97 for a hand. It is appreciated that the implementation illustrated is only exemplary and that more than two emitter/detector pairs is possible.

Returning to FIG. 1, pressure device 114 may be configured to provide a pressure signal conveying information associated with an ambient air pressure in an environment surrounding apparatus 102. The pressure device 114 may include a barometer, an altimeter, and/or other devices configured to facilitate determining ambient air pressure.

The user interface 116 may be configured to facilitate interactions between apparatus 102 and a user. Such interactions may include providing information to and receiving information from the user. Examples of interface devices suitable for inclusion in user interface 108 may include a keypad, buttons, switches, a keyboard, knobs, levers, a display screen, a touch screen, speakers, a microphone, an indicator light, an audible alarm, a printer, and/or other user interfaces. The information provided by user interface 116 may include $SpO_2$ (oxygen saturation), heart rate, arterial pulse waveforms, representations of normal $SpO_2$ range relative to measured values, user instructions, quality and strength of the pulse signals, the presence of CHD, and/or other information.

In some implementations, user interface 116 may include a barcode scanner configured to scan a barcode. The barcode may include a matrix barcode (e.g., a QR code), a two-dimensional barcode, a linear barcode, and/or other optically scannable graphical code. The barcode may be associated with the newborn. For example, the barcode may be disposed on wristband worn by the newborn, an ankle band worn by the newborn, and/or a printed medical chart. The barcode may associated with an identity of the newborn, a medical record of the newborn, an electronic medical record (EMR) of the newborn, and/or other information associated with the newborn. The user interface 116 may include other scanners. For example, user interface 116 may include an identification band scanner configured to scan an identification band worn by the newborn. In some implementations, the identification band scanner may include a radio-frequency identification device scanner. In some implementations, user interface 116 may include a plurality of separate interfaces.

It is to be understood that other communication techniques, either hard-wired or wireless, are contemplated by the present disclosure as user interface 116. For example, the present disclosure contemplates that user interface 116 may be integrated with a removable storage interface. In this example, information may be loaded into system 100 from removable storage (e.g., a smart card, a flash drive, a removable disk, etc.) that enables the user(s) to customize the implementation of system 100. Other exemplary input devices and techniques adapted for use with system 100 as user interface 116 include, but are not limited to, an RS-232 port, RF link, an IR link, modem (telephone, cable, and/or other). In short, any technique for communicating information with system 100 is contemplated by the present disclosure as user interface 108.

The sensor positioning device 118 may be configured to reposition individual ones of the two or more sensor pairs 112. A given sensor pair 112 may be repositioned responsive to the portion of the newborn's hand or foot being received by the cavity of body 110. Repositioning a given sensor pair may include moving one or both of the light emitter or the light detector of the given sensor pair such that one or both of the light emitter or the light detector contact skin on the portion of the newborn's hand or foot that is within the cavity. In some implementations, one or both of the light emitter or the light detector of a given sensor pair may be moved along an axis that passes through both the light emitter and the light detector. Lateral alignment between the light emitter and the light detector of a given sensor pair may be maintained after being adjusted such that, after moving one or both of the light emitter or the light detector, light from the light emitter that passes through the newborn's hand or foot within the cavity is detected by the light detector. The sensor positioning device 118 may include one or more of a spring, a cushion, a motor, and/or other devices configured to reposition one or both of the light emitter or the light detector of a given sensor pair.

Turning again to FIG. 9, in one implementation, each emitter and detector is connected to an interior wall of chamber 10 with sensor positioning device 101, which may be the same as or similar to sensor positioning device 118 in FIG. 1. The sensor positioning device 101 can adjust, permit adjustment of, or prevent adjustment of, the physical location of emitters and detectors within chamber 10 of apparatus 5. That is, in one implementation, each emitter and each detector is adjustably projectable within chamber 10 of apparatus 5. The sensor positioning device 101 help to optimize apparatus 5 performance by improving or maintaining sensor alignment, sensor position, and signal acquisition. In one implementation, the position of each emitter and detector can be adjusted, altered, or maintained so that contact with a newborn extremity is improved, sustained, or otherwise optimized. Sensor positions can be maintained, for example, when good contact is made with a newborn's hand or foot prior to adjustment. In such a case, apparatus 5 can prevent adjustment to help sustain, or preserve, the contact that is made with the newborn's extremity. In another implementation, the position of each emitter and detector can be changed such that their proximity to a newborn extremity is improved, maintained, or otherwise optimized. For example, in cases where one or more sensors do not make contact with a newborn's hand or foot, the sensor can be adjusted toward the hand or foot to acquire better signal quality, even if such adjustment does not result in contact with the newborn's hand or foot. It is appreciated that sensor positions can be optimized, or adjusted, by moving sensors toward and away from a newborn's hand or foot.

Not having sufficient contact with a newborn's hand or foot makes pulse oximeter screening take longer and it decreases the resulting signal quality. The sensor positioning device 101 help to ameliorate the problems that arise when sensors make poor contact with a newborn's hand or foot by improving, maintaining, or otherwise optimizing apparatus 5 sensor positions. However, it is appreciated that too much sensor contact with a newborn's hand or foot can cause problems as well, just as too little contact can. Too much contact can cause a newborn discomfort and unduly stress the sensors. Thus, sensor positioning device 101 can also be used to help ensure newborn comfort during the screening process and to help reduce the mechanical stress placed on the sensors so that the lifespan of apparatus 5 and apparatus 5 components, including the sensors and approximating mechanisms, are prolonged, and if not prolonged, at least not diminished.

The sensor positioning device 101 can be a spring, a motorized arm, a cushion, or any elastic or inelastic mechanism, composed of one or more parts, that can adjust the position of the emitter or detector. It is appreciated that adjustment can be accomplished automatically, manually, or in some combination thereof. Regardless, in one implementation, adjustment can be accomplished in relation to the attachment point of sensor positioning device 101 to a wall of chamber 10. The sensor positioning device 101 can adjust a sensor in a variety of ways. For example, sensor adjustment can include a combination of translational and rotational movement. In one implementation, translational movement can include movement perpendicular to and movement lateral to the attachment point of sensor positioning device 101. Perpendicular movement can include compression toward and extension from a wall of chamber 10. Lateral movement can include planar movement perpendicular to the plane in which compression or extension occurs. In one implementation, rotational movement can include changing the angle of a sensor in relation to a wall of chamber 10. For example, a sensor angle can be changed such that the sensor surface is parallel with, or becomes more parallel with, the anatomical surface that it makes contact with. In other words, in one implementation, each emitter and detector can have six degrees of freedom. That is, in one implementation, sensor movement can include translational movement along traditional X, Y, and Z axes, or along other similar axes, and rotational movement about those traditional axes, or about those other similar axes. Those of skill in the art will understand that five or less degrees of freedom is possible as well.

In addition, in one implementation, sensor positioning device 101 can have limited adjustment capability. That is, the range of movement of each sensor can be limited or constrained by restricting the amount of adjustment that is permitted. For example, in one implementation, translational movement can be limited to one centimeter, measured from a neutral position, along any one of a traditional X, Y, or Z axis, or plane. In another implementation, rotational movement can, for example, be limited to ten degrees, measured from a neutral position, about any one of a traditional X, Y, or Z axis. Limiting the range of sensor movement by limiting the range of possible adjustment helps to ensure that each emitter/detector is sufficiently aligned with their respective detector and emitter to properly pass light through a newborn extremity and acquire good signal quality.

Moreover, the position of the sensors can be adjusted collectively (i.e., all adjustments for the different sensors are equivalent), individually (i.e., all adjustments for the different sensors are unique), or in some combination thereof. For example, in an implementation where sensor positioning device 101 for each emitter/receiver is a spring that is adjusted manually (e.g., a compression spring), placement of a newborn's hand or foot against the emitter or receiver is sufficient to impart translational sensor movement (e.g., move an emitter, a receiver, or both closer to a wall of chamber 10). In such an implementation, each sensor adjustment is unique. That is, each spring is compressed a different amount depending on the amount of mechanical force a newborn's hand or foot applies against each spring when inserted into chamber 10. In another implementation, movement of each emitter and detector can be synchronized in the lateral direction but not necessarily in the perpendicular direction. In another implementation, the approximating mechanism used for each individual sensor can vary (e.g., a spring can be used for the emitter/detector pair 22/32 and a gel cushion can be used for the emitter/detector pair 88/98).

The sensor positioning device 101 can have one or more neutral, or home, positions. For example, in one implementation, apparatus 5 can include preset home positions for small, medium, and large newborn feet and hands. In such an implementation, a user can select a hand or foot size (e.g., large) prior to inserting the hand or foot into chamber 10. For example, if a user selects a large foot size, the sensors of apparatus 5 can, in one implementation, automatically move toward the walls of chamber 10 to help accommodate the larger foot. Once a foot is inserted after the sensors self-adjust, the sensors can further adjust, as previously discussed, to improve or maintain sensor alignment, sensor position, and signal acquisition. In another implementation, the sensors can adjust or continue to adjust as the foot is inserted. Preselecting a hand or foot size can save time by preventing the need to insert a hand or foot into chamber 10 multiple times for a single screening in an effort to acquire good signal quality. Preselecting a hand or a foot can also reduce wear and tear on the sensors because it can reduce the number of times a newborn extremity is inserted into chamber 10 and it can prevent large hands or feet from exerting too much mechanical force on the sensors.

In one implementation, sensor positioning device 101 can include locking mechanisms that lock the sensors and corresponding adjustment mechanisms into place. In one implementation, sensors can be locked into position when device 5 screening measurements are initiated. In another implementation, sensors can be locked into position before a hand or foot is inserted. In yet another implementation, sensors can be locked into place after sensor positioning device 101 adjust the sensor positions but before screening measurements are initiated. It is appreciated that other locking timeframes are possible. A benefit of locking sensors in place during the pulse oximeter screening is that it can prevent or reduce motion artifacts. Other benefits are also appreciated.

Turning again to FIG. 1, some implementations of system 100 may include a disposable cover 120. The disposable cover 120 may be configured to line the cavity of apparatus 102 to protect skin on the portion of the newborn's hand or foot that is received by the cavity. The disposable cover 120 may include transparent portions and opaque portions. The transparent portions may be configured to allow light to pass between individual sensor pairs 112. The opaque portions may be configured to block light from passing between adjacent sensor pairs 112. In some implementations, an applicator (not depicted) may be configured to position disposable cover 120 within the cavity of apparatus 102 such that a given transparent portion of disposable cover 120 is aligned with a given sensor pair 112. The disposable cover may be configured to be held in position within the cavity by one or more of static cling, a gel, an adhesive, a hook-and-loop fastener, a snap fastener, a clip, and/or other techniques for temporarily securing disposable cover 120. The disposable cover 120 may comprise a rigid or semi-rigid ring that corresponds to an opening of the cavity. Such a ring may aid in securing disposable cover within the cavity. In some implementations, disposable cover 120 may conform to an internal shape of the cavity.

FIG. 10 illustrates an exemplary implementation of a disposable cover 70, which may be the same as or similar to disposable cover 120 in FIG. 1. The disposable cover 70 may be shaped to fit within the interior of device 5 (in chamber 10) before placing a newborn's foot or hand into chamber 10. The disposable cover 70 may be made of a thin polyurethane membrane and shaped to fit the interior of the device. According to various implementations, the membrane can be uniformly translucent or translucent in the twelve locations that correspond to the locations of the six pairs of light emitters 21, 22, 23, 87, 88, 89 and their respective receivers 31, 32, 33, 97, 98, 99 of the device. FIG. 10 shows six translucent locations 71, 72, 73, 74, 75, 76 that correspond to the six emitters 21, 22, 23, 87, 88, 89. The six translucent locations that correspond to the six receivers 31, 32, 33, 97, 98, 99 are not visible from this perspective. By using a design where only the twelve locations of the membrane are translucent, there is a reduction in potential "noise" and the chance of optical detector saturation from ambient lights. It can also minimize light scattering from the interior of the unit from emitters in one channel to the receiver of another channel. As shown in FIG. 10, in one embodiment, disposable cover 70 includes plastic ring 77 at the end opening of disposable cover 70 to provide a shape of the cover similar to a shape of chamber 10 of device 5. An applicator can be used for easy placement of disposable cover 70 into device 5. The disposable cover 70 can be impermeable to microorganisms and pre-sterilized to protect against infection. Adhesives do not need to be applied to the side of the membrane that makes contact with the skin to avoid irritation because the cover is composed of material (e.g., polyurethane) that does not irritate the skin. Polyurethane material such as Tegaderm® (3M) has been used extensively in newborns with very low rate of skin irritation or allergy.

Referring again to FIG. 1, apparatus 102 may be configured to execute one or more computer program modules. The computer program modules may include one or more of an oxygen saturation determination module 122, a CHD determination module 124, a pressure determination module 126, a threshold adjustment module 128, an EMR interface module 130, a sensor selection module 132, a sensor positioning module 134, and/or other modules.

The oxygen saturation determination module 122 may be configured to determine a saturation value indicative of oxygen saturation of the newborn. The saturation value may be determined based on one or more detection signals provided by sensor pairs 112.

The CHD determination module 124 may be configured to determine a presence of CHD in the newborn. Such a determination may be made responsive to the saturation value breaching a threshold saturation value. According to some implementations, at or near sea level, a screen result would be considered a pass (i.e., a negative screen for CHD) for any screening with an oxygen saturation measure that is greater than or equal to ninety-five percent in either extremity with an absolute difference in oxygen saturation between the upper and lower extremity less than or equal to three percent. A screen result may be considered a fail (i.e., a positive screen for CHD) if (1) any oxygen saturation measure is less than ninety percent, (2) oxygen saturation is less than ninety-five percent in both extremities on three measures, each separated by one hour, or (3) there is a greater than three percent absolute difference in oxygen saturation between the right hand and foot on three measures, each separated by one hour. The algorithm for pass or fail of CHD screening can be adjusted as new guidelines for CHD screening from Centers for Disease Control and Prevention (CDC) become available. The pass/fail CHD screening algorithm can vary in a number of ways. For example, the $SpO_2$ percentage cutoffs used in the algorithm can be dynamic rather than static thresholds. Dynamic means that the percentage cutoff is not preset, or if it is preset, that it can be changed either automatically or manually.

The pressure determination module 126 may be configured to determine the ambient air pressure, or barometric pressure, in the environment surrounding the apparatus. The ambient air pressure may be determined based on the pressure signal provided by pressure device 114. In some implementations, the ambient air pressure may be determined at prior to each use of apparatus 102, on a weekly basis, on an annual basis, and/or according to some other timing scheme. In some implementations, the ambient air pressure may be determined only occasionally such as prior to the first use of apparatus 102, during calibration of apparatus 102, when apparatus 102 is moved to a different location (e.g., a different city, state, country, etc.), and/or at other times.

The threshold adjustment module 128 may be configured to adjust the threshold saturation value. The threshold saturation value may be adjusted based on the ambient air pressure and/or geo-location information to reduce a probability of false positives attributable to high-altitude environments. Normal $SpO_2$ percentage, like barometric pressure, decreases as elevation increases. In some implementations, threshold adjustment module 128 may be configured to adjust the threshold saturation value downward for ambient air pressures that are lower than atmospheric pressure at sea level. For example, a threshold saturation value of 95% oxygen saturation may be appropriate at sea level, while a threshold saturation value of 93% oxygen saturation may be more appropriate in Denver where the ambient air pressure is lower than at sea level. In some implementations, the threshold saturation value adjustment may be customized such as by adjustment by a user. In some implementations, ambient air pressure can be measured automatically before every screening or at other intervals such as preset, but modifiable, timeframes. In some implementations, ambient air pressure may be determined responsive to a user instruction being provided to apparatus 102 (e.g., a user can initiate a pressure calibration sequence).

The EMR interface module 130 may be configured to access and/or manage an electronic medical record (EMR) associated with newborns. An EMR may include an electronic health record (EHR), an electronic patient record (EPR), and/or other medical or health records that are electronically stored and accessed. The EMR may comprise a systematic collection of electronic health information about individual newborns in digital format. The EMR may be capable of being shared across different health care settings. In some implementations, this sharing can occur by way of network-connected, enterprise-wide information systems, and/or other information networks or exchanges. The EMR may include a range of information including demographics, medical history, medication and allergies, immunization status, CHD screening results, laboratory test results, radiology images, vital signs, personal statistics (e.g., weight), billing information, and/or other information.

The EMR interface module 130 may be configured to store information associated with oxygen saturation of the newborn in the EMR associated with the newborn. The EMR interface module 130 may be configured to transfer screening results to an EMR system in real time or near-real time. The EMR interface module 130 may be configured to storing screening results of several newborns at apparatus 102, and send those results to an EMR system in a batch, on demand, automatically, when connected to an EMR system via wireline or wirelessly, according to a custom schedule, and/or at other times and/or frequencies.

In some implementations, EMR interface module 130 may be configured to provide one or more alerts directed to one or more caregivers. Such an alert may be realized as a local alarm (e.g., an alarm at or near apparatus 102), a text message, an email message, an alert provided via a portable digital device (e.g., pager or cellular phone), and/or other alerts. An alert may be provided responsive to a critical reading obtained by apparatus 102. For example, EMR interface module 130 may be configured to effectuate provision of an alert directed to a healthcare provider responsive to a positive determination of a presence of CHD in the newborn. The EMR interface module 130 may be configured to provide a recommendation responsive to a failed screening. The recommendation may convey that a rescreen should be performed according to established guidelines. Such guidelines may be set forth by the Centers for Disease Control, the American Academy of Pediatrics, hospital guidelines, guidelines established by a specific doctor or other healthcare provider, and/or other organizations or individuals.

The sensor selection module 132 may be configured to select a subset of the detection signals provided by sensor pairs 112 based on which body part of the newborn is received by the cavity (e.g., a portion of a left foot, a right foot, a left hand, or a right hand). In order to determine the subset, sensor pairs 112 may be configured to perform scans simultaneously, to perform scans cyclically one sensor pair 112 at a time, and/or according to another scheme. The detection signals from sensor pairs 112 may be compared, and the best signals (e.g., strongest and most uniform) may be included in the subset. Responsive to the newborn's foot or hand moving, and thereby losing the sensor position, the sensor pairs 112 may automatically resume scanning so that the best detection signals can again be determined.

The sensor positioning module 134 may be configured to control the sensor positioning device 118 to reposition individual ones of the two or more sensor pairs 112 responsive to the portion of the newborn's hand or foot being received by the cavity. As discussed above, repositioning a given sensor pair 112 may include moving one or both of the light emitter or the light detector of the given sensor pair 112 such that one or both of the first light emitter or the first light detector contact skin of the portion of the newborn's hand or foot.

In some implementations, apparatus 102, client computing platform(s) 104, server(s) 106, portable digital device(s) 108, and/or external resources 136 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which apparatus 102, client computing platform(s) 104, server(s) 106, portable digital device(s) 108, and/or external resources 136 may be operatively linked via some other communication media.

A given client computing platform 104 may include one or more processors configured to execute computer program modules (e.g., modules 122, 124, 126, 128, 130, 132, 134, and/or other modules). The computer program modules may be configured to enable an expert or user associated with the given client computing platform 104 to interface with system 100 and/or external resources 136, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, and/or other computing platforms.

A given server 106 may include one or more processors configured to execute computer program modules (e.g., modules 122, 124, 126, 128, 130, 132, 134, and/or other modules). The computer program modules may be configured to enable an expert to interface with system 100 and/or external resources 136, and/or provide other functionality attributed herein to server(s) 106.

A given portable digital device 108 may include one or more processors configured to execute computer program modules (e.g., modules 122, 124, 126, 128, 130, 132, 134, and/or other modules). The computer program modules may be configured to enable an expert or user associated with the given client computing platform 104 to interface with system 100 and/or external resources 136, and/or provide other functionality attributed herein to portable digital device(s) 108. By way of non-limiting example, the given portable digital device 108 may include one or more of a pager, a cellular phone, and/or other portable digital devices.

External resources 136 may include sources of information, hosts and/or providers of EMR outside of system 100, external entities participating with system 100, and/or other resources. In some implementations, some or all of the functionality attributed herein to external resources 136 may be provided by resources included in system 100.

The apparatus 102 may include electronic storage 138, one or more processors 140, and/or other components. The apparatus 102 may include communication lines, or ports to enable the exchange of information with a network and/or other computing platforms or devices. Illustration of apparatus 102 in FIG. 1 is not intended to be limiting. The apparatus 102 may include a plurality of hardware, software, and/or firmware components operating together to provide the functionality attributed herein to apparatus 102. For example, apparatus 102 may be implemented by a cloud of computing platforms operating together as apparatus 102.

Electronic storage 138 may comprise non-transitory storage media that electronically stores information. The electronic storage media of electronic storage 138 may include one or both of system storage that is provided integrally (i.e., substantially non-removable) with apparatus 102 and/or removable storage that is removably connectable to apparatus 102 via, for example, a port (e.g., a USB port, a firewire port, etc.) or a drive (e.g., a disk drive, etc.). Electronic storage 138 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 138 may include one or more virtual storage resources (e.g., cloud storage, a virtual private network, and/or other virtual storage resources). Electronic storage 138 may store software algorithms, information determined by processor(s) 140, information received from client computing platform(s) 104, information received from server(s) 106, information received from portable digital device(s) 108, and/or other information that enables apparatus 102 to function as described herein.

The processor(s) 140 is configured to provide information processing capabilities in apparatus 102. As such, processor(s) 140 may include one or more of a digital processor, an analog processor, a digital circuit designed to process information, an analog circuit designed to process information, a state machine, and/or other mechanisms for electronically processing information. Although processor(s) 140 is shown in FIG. 1 as a single entity, this is for illustrative purposes only. In some implementations, processor(s) 140 may include a plurality of processing units. These processing units may be physically located within the same device, or processor(s) 140 may represent processing functionality of a plurality of devices operating in coordination. The processor(s) 140 may be configured to execute modules 122, 124, 126, 128, 130, 132, 134, and/or other modules. The processor(s) 140 may be configured to execute modules 122, 124, 126, 128, 130, 132, 134, and/or other modules by software; hardware; firmware; some combination of software, hardware, and/or firmware; and/or other mechanisms for configuring processing capabilities on processor(s) 140. As used herein, the term "module" may refer to any component or set of components that perform the functionality attributed to the module. This may include one or more physical processors during execution of processor readable instructions, the processor readable instructions, circuitry, hardware, storage media, and/or any other components.

It should be appreciated that although modules 122, 124, 126, 128, 130, 132, and 134 are illustrated in FIG. 1 as being implemented within a single processing unit, in implementations in which processor(s) 140 includes multiple processing units, one or more of modules 122, 124, 126, 128, 130, 132, and/or 134 may be implemented remotely from the other modules. The description of the functionality provided by the different modules 122, 124, 126, 128, 130, 132, and/or 134 described below is for illustrative purposes, and is not intended to be limiting, as any of modules 122, 124, 126, 128, 130, 132, and/or 134 may provide more or less functionality than is described. For example, one or more of modules 122, 124, 126, 128, 130, 132, and/or 134 may be eliminated, and some or all of its functionality may be provided by other ones of modules 122, 124, 126, 128, 130, 132, and/or 134. As another example, processor(s) 140 may be configured to execute one or more additional modules that may perform some or all of the functionality attributed below to one of modules 122, 124, 126, 128, 130, 132, and/or 134.

Figure 11:
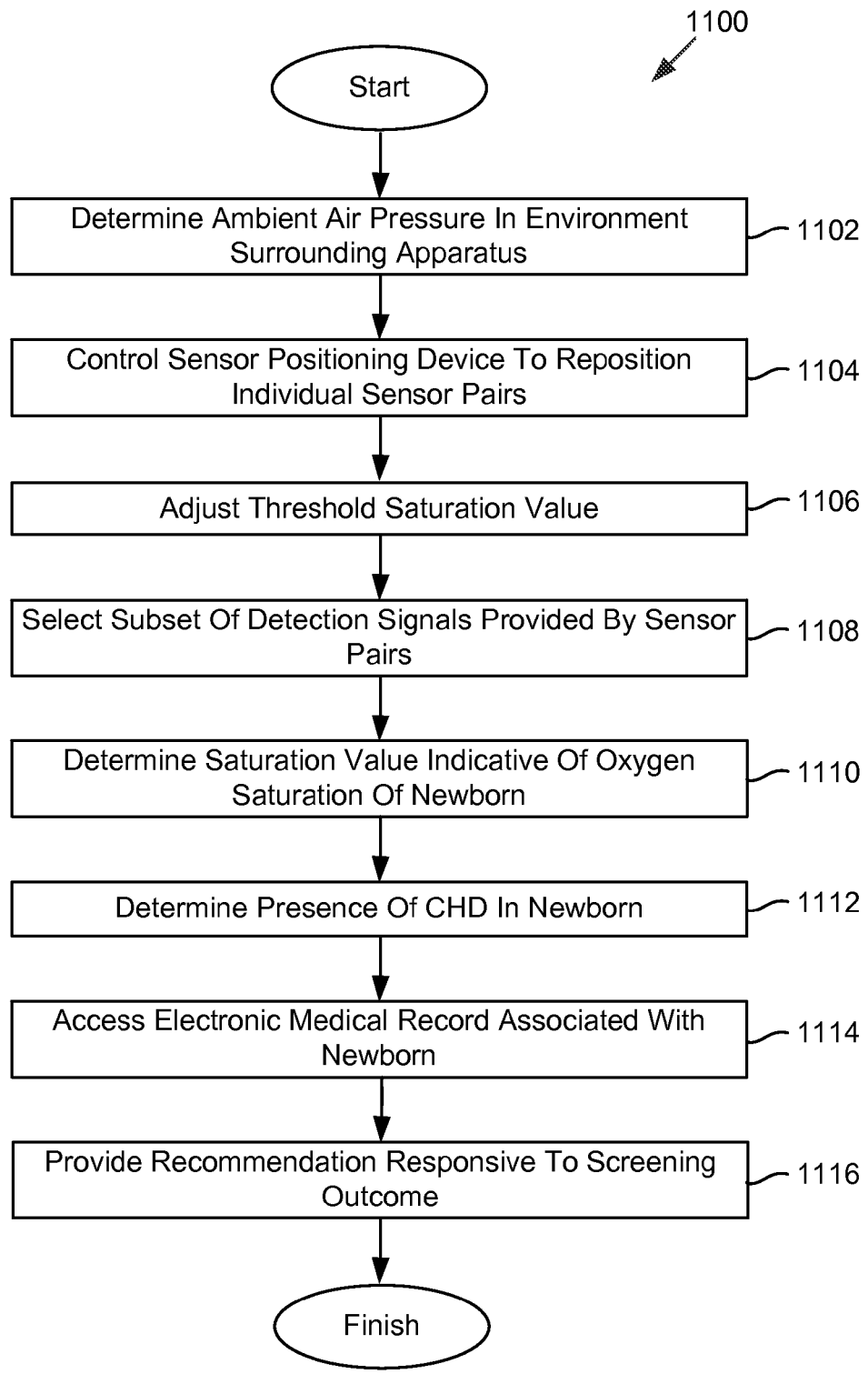
FIG. 11 illustrates a method for detecting CHD in newborns, in accordance with one or more implementations.

FIG. 11 illustrates a method 1100 for detecting CHD in newborns, in accordance with one or more implementations. The operations of method 1100 presented below are intended to be illustrative. In some implementations, method 1100 may be accomplished with one or more additional operations not described, and/or without one or more of the operations discussed. Additionally, the order in which the operations of method 1100 are illustrated in FIG. 11 and described below is not intended to be limiting.

In some implementations, some or all of method 1100 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1100 in response to instructions stored electronically on an electronic storage medium. The one or more processing devices may include one or more devices configured through hardware, firmware, and/or software to be specifically designed for execution of one or more of the operations of method 1100.

At an operation 1102, the ambient air pressure in the environment surrounding an apparatus (e.g., apparatus 102) may be determined based on the pressure signal provided by a pressure device (e.g., pressure device 114). Operation 1102 may be performed by one or more processors configured to execute a pressure determination module that is the same as or similar to pressure determination module 126, in accordance with one or more implementations.

At an operation 1104, a sensor positioning device (e.g., sensor positioning device 118) may be controlled to reposition individual ones of the two or more sensor pairs responsive to the portion of the newborn's hand or foot being received by the cavity. Repositioning a given sensor pair may include moving one or both of the light emitter or the light detector of the given sensor pair such that one or both of the first light emitter or the first light detector contact skin of the portion of the newborn's hand or foot. Operation 1104 may be performed by one or more processors configured to execute a sensor positioning module that is the same as or similar to sensor positioning module 134, in accordance with one or more implementations.

At an operation 1106, the threshold saturation value may be adjusted based on the ambient air pressure to reduce a probability of false positives attributable to high-altitude environments. Operation 1106 may be performed by one or more processors configured to execute a threshold adjustment module that is the same as or similar to threshold adjustment module 128, in accordance with one or more implementations.

At an operation 1108, a subset of the detection signals provided by the sensor pairs may be selected based on which body part of the newborn is received by the cavity. The body part may be a portion of one of a left foot, a right foot, a left hand, or a right hand. Operation 1108 may be performed by one or more processors configured to execute a sensor selection module that is the same as or similar to sensor selection module 132, in accordance with one or more implementations.

At an operation 1110, a saturation value indicative of oxygen saturation of the newborn may be determined based on one or more detection signals provided by two or more sensor pairs (e.g., sensor pairs 112). Operation 1110 may be performed by one or more processors configured to execute an oxygen saturation determination module that is the same as or similar to oxygen saturation determination module 122, in accordance with one or more implementations.

At an operation 1112, a presence of CHD in the newborn may be determined responsive to the saturation value breaching a threshold saturation value. Operation 1112 may be performed by one or more processors configured to execute a CHD determination module that is the same as or similar to CHD determination module 124, in accordance with one or more implementations.

At an operation 1114, an electronic medical record associated with the newborn may be accessed. Operation 1114 may be performed by one or more processors configured to execute an EMR interface module that is the same as or similar to EMR interface module 130, in accordance with one or more implementations.

At an operation 1116, a recommendation may be provided responsive to the screening. For example, a recommendation may be provided responsive to a failed screening. The recommendation may convey that a rescreen should be performed according to established guidelines. Such guidelines may be set forth by the Centers for Disease Control, the American Academy of Pediatrics, hospital guidelines, guidelines established by a specific doctor or other healthcare provider, and/or other organizations or individuals. Examples of other recommendations may include an indication that the screening was passed and that no rescreen is necessary, that the screening was failed and that an echocardiogram is recommended, and/or other recommendations. Operation 1116 may be performed by one or more processors configured to execute an EMR interface module that is the same as or similar to EMR interface module 130, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. Apparatus configured to detect CHD in newborns, the apparatus comprising:
   a body comprising a cavity configured to receive a portion of a hand or a foot of a newborn, the cavity substantially encompassing the portion of the newborn's hand or foot when the portion of the newborn's hand or foot is received by the cavity;
   sensor pairs including a first sensor pair, individual ones of the two or more sensor pairs being configured to provide detection signals conveying information associated with oxygen saturation, the first sensor pair including a first light emitter and a corresponding first light detector disposed at opposing locations in the cavity of the body such that, when the portion of the newborn's hand or foot is inside the cavity, light from the first light emitter that passes through the newborn's hand or foot is detected by the first light detector;
   one or more hardware processors configured by machine-readable instructions to:
   select a subset of the detection signals provided by the sensor pairs based on a determination of which body part of the newborn is received by the cavity, the body part being a portion of one of a left foot, a right foot, a left hand, or a right hand;
   determine a saturation value indicative of oxygen saturation of the newborn based on the selected subset of the detection signals, wherein the saturation value is determined based on one or more detection signals provided by the sensor pairs;
   determine a presence of CHD in the newborn responsive to the saturation value breaching a threshold saturation value, wherein the presence of CHD is determined responsive to the saturation value breaching a threshold saturation value; and
   determine an ambient air pressure in the environment surrounding the apparatus based on a pressure signal provided by a pressure device; and
   a sensor positioning device configured to reposition individual ones of the two or more sensor pairs responsive to the portion of the newborn's hand or foot being received by the cavity, wherein repositioning the first sensor pair includes a combination of transitional and rotational movement configured to move one or both of the first light emitter or the first light detector such that one or both of the first light emitter or the first light detector configured to contact skin of the portion of the newborn's hand or foot, wherein the sensor positioning device includes one or more of a spring, a cushion, an elastic mechanism, an inelastic mechanism, a motorized arm, or a motor configured to adjust, by repositioning, automatically, manually, or in some combination thereof, one or both of the first light emitter or the first light detector of a sensor pair, wherein the adjustment is accomplished in relation to an attachment point of the sensor positioning device, wherein the sensor positioning device is configured to adjust a sensor using the combination of translational and rotational movement, wherein translational movement includes one or more of movement perpendicular to or movement lateral to the attachment point of the sensor positioning device, wherein perpendicular movement includes compression toward and extension from a wall, wherein lateral movement includes planar movement perpendicular to the plane in which compression or extension occurs, wherein rotational movement includes changing the angle of a sensor in relation to the wall, and wherein the sensor pair is configured to be repositioned responsive to the portion of the newborn's hand or foot being received by the cavity of body, wherein repositioning the sensor pair includes moving one or both of the light emitter or the light detector of the sensor pair such that one or both of the light emitter or the light detector configured to contact skin on the portion of the newborn's hand or foot that is within the cavity wherein one or both of the first light emitter or the first light detector of the given sensor pair may be moved along an axis that passes through both the light emitter and the light detector, and wherein lateral alignment between the light emitter and the light detector of the sensor pair is maintained after being adjusted.

2. The apparatus of claim 1, wherein the sensor pairs are configured to perform scans simultaneously.

3. The apparatus of claim 1, wherein the sensor pairs are configured to perform scans cyclically one sensor pair at a time.

4. The apparatus of claim 1, wherein the one or more hardware processors are further configured by machine-readable instructions such that the threshold saturation value is adjusted based on the ambient air pressure to reduce a probability of false positives attributable to high-altitude environments.

5. The apparatus of claim 1, wherein the one or more hardware processors are further configured by machine-readable instructions such that the threshold saturation value is adjusted downward for ambient air pressures that are lower than atmospheric pressure at sea level.

6. The apparatus of claim 1, wherein the one or more hardware processors are further configured by machine-readable instructions to access an EMR associated with the newborn.

7. The apparatus of claim 1, further including a disposable cover configured to line the cavity to protect skin on the portion of the newborn's hand or foot that is received by the cavity, the disposable cover including transparent portions and opaque portions, the transparent portions being configured to allow light to pass between individual sensor pairs, the opaque portions being configured to block light from passing between adjacent sensor pairs.

* * * * *